(12) United States Patent
Kubotani et al.

(10) Patent No.: US 9,105,172 B2
(45) Date of Patent: Aug. 11, 2015

(54) DROWSINESS-ESTIMATING DEVICE AND DROWSINESS-ESTIMATING METHOD

(75) Inventors: Hiroyuki Kubotani, Hyogo (JP); Hiroki Kitajima, Kanagawa (JP)

(73) Assignee: PANASONIC CORPORATION, Osaka (JP)

( * ) Notice: Subject to any disclaimer, the term of this patent is extended or adjusted under 35 U.S.C. 154(b) by 110 days.

(21) Appl. No.: 14/118,361

(22) PCT Filed: May 25, 2012

(86) PCT No.: PCT/JP2012/003411
§ 371 (c)(1),
(2), (4) Date: Nov. 18, 2013

(87) PCT Pub. No.: WO2012/160830
PCT Pub. Date: Nov. 29, 2012

(65) Prior Publication Data
US 2014/0062704 A1    Mar. 6, 2014

(30) Foreign Application Priority Data

May 26, 2011 (JP) ................................. 2011-117834

(51) Int. Cl.
*G08B 23/00* (2006.01)
*G08B 21/06* (2006.01)
(Continued)

(52) U.S. Cl.
CPC .............. *G08B 21/06* (2013.01); *A61B 5/1079* (2013.01); *A61B 5/1128* (2013.01); *A61B 5/18* (2013.01); *G06K 9/00845* (2013.01); *A61B 5/1121* (2013.01)

(58) Field of Classification Search
CPC ........ G08B 21/06; A61B 5/1079; A61B 5/18; G06K 9/00845
USPC ....................................... 340/575, 576, 573.1
See application file for complete search history.

(56) References Cited

U.S. PATENT DOCUMENTS 4,928,090 A * 5/1990 Yoshimi et al. ................ 340/575
5,311,877 A * 5/1994 Kishi ............................. 600/545
(Continued)

FOREIGN PATENT DOCUMENTS

| JP | 2007-229218 A | 9/2007 |
| JP | 2009-045418 A | 3/2009 |
| JP | 2010-253033 A | 11/2010 |

OTHER PUBLICATIONS

"Prediction of Automobile Driver Sleepiness" The Japan Society of Mechanical Engineers (C edition), vol. 63, No. 613, pp. 93-100, 1997.

(Continued)

*Primary Examiner* — Eric M Blount
(74) *Attorney, Agent, or Firm* — Pearne & Gordon LLP

(57) ABSTRACT

A drowsiness-estimating device capable of improving the precision of drowsiness estimation by eliminating the effect of individual differences. In the device, a recurrence required time-calculating part (103) calculates the recurrence required time, which is the time needed, after a detection time when an action is detected, for a drowsiness estimation parameter value acquired after the detection time to return to the value of the drowsiness estimation parameter acquired before the detection time. A drowsiness-estimating part (104) estimates the level of drowsiness of the drowsiness-estimation subject on the basis of the calculated recurrence required time. To be specific, the drowsiness-estimating part (104) maintains a drowsiness level-estimating table in which each of multiple time ranges is correlated with a possible drowsiness level, and specifies a possible drowsiness level that corresponds to the time range, among the multiple time ranges, with which the recurrence required time is associated.

7 Claims, 13 Drawing Sheets

(51) Int. Cl.
  *A61B 5/107* (2006.01)
  *A61B 5/11* (2006.01)
  *A61B 5/18* (2006.01)
  *G06K 9/00* (2006.01)

(56) References Cited

U.S. PATENT DOCUMENTS

| | | | |
|---|---|---|---|
| 5,786,765 A * | 7/1998 | Kumakura et al. | 340/576 |
| 7,791,491 B2 * | 9/2010 | Johns | 340/576 |
| 8,040,247 B2 * | 10/2011 | Gunaratne | 340/575 |
| 8,154,591 B2 * | 4/2012 | Morita et al. | 348/78 |
| 8,369,608 B2 * | 2/2013 | Gunaratne | 382/154 |
| 8,823,792 B2 * | 9/2014 | Omi | 348/135 |
| 2004/0234103 A1 * | 11/2004 | Steffein | 382/104 |
| 2006/0232430 A1 * | 10/2006 | Takaoka et al. | 340/575 |
| 2008/0068186 A1 * | 3/2008 | Bonefas et al. | 340/575 |
| 2008/0212828 A1 | 9/2008 | Ishida et al. | |
| 2009/0261979 A1 * | 10/2009 | Breed et al. | 340/576 |
| 2014/0097957 A1 * | 4/2014 | Breed et al. | 340/576 |

OTHER PUBLICATIONS

International Search Report for PCT/JP2012/003411 dated Jul. 17, 2012.

* cited by examiner

| | SIZE OF DRIVING ACTION | | |
|---|---|---|---|
| | SMALL | MEDIUM | LARGE |
| t_1 | a_1 | b_1 | c_1 |
| t_2 | a_2 | b_2 | c_2 |
| t_3 | a_3 | b_3 | c_3 |

FIG. 10

| DRIVING EVENT | | | |
|---|---|---|---|
| NO | YES | | |
| | HIGH | LOW | |
| t_1 | d_1 | e_1 | f_1 |
| t_2 | d_2 | e_2 | f_2 |
| t_3 | d_3 | e_3 | f_3 |

FIG. 13

DROWSINESS-ESTIMATING DEVICE AND DROWSINESS-ESTIMATING METHOD

TECHNICAL FIELD

The present invention relates to a drowsiness-estimating apparatus and a drowsiness-estimating method.

BACKGROUND ART

In order to prevent the driver of a vehicle from falling asleep at the wheel, a device has been proposed for capturing a facial image of the driver using a camera mounted near the driver's seat and estimating the drowsiness of the driver based on a captured facial image (for example, in Patent Literature 1). This apparatus, using the captured facial image, measures a drowsiness characteristic quantity of the distance between a plurality of feature points (that is, feature regions on a face), the tilt of the head, or the like, and estimates the drowsiness based on the difference between the drowsiness characteristic quantity when awake (hereinafter sometimes referred to as "reference characteristic quantity") and the drowsiness characteristic quantity when drowsiness is estimated.

The drowsiness determining device disclosed in Patent Literature 1, with regard to expression information indicating the distance and angle between various parts of the face, compares the expression information at a first timing and the expression information at a second timing, and judges the occurrence of drowsiness based on the magnitude relationship of the expression information.

CITATION LIST

Patent Literature

PTL 1
Japanese Patent Application Laid-Open No. 2009-45418
Non-Patent Literature
Non-Patent Literature 1: "Prediction of Automobile Driver Sleepiness" The Japan Society of Mechanical Engineers (C edition), Vol. 63, No. 613, pp 93-100, 1997.

SUMMARY OF INVENTION

Technical Problem

However, there are differences in the manner in which drowsiness manifests itself in expressions, and the value of expression information, which is the reference for judging the drowsiness level, differs depending upon the individual person. As a result, it is difficult to detect drowsiness without the influence of differences between individuals.

An object of the present invention is to provide a drowsiness-estimating apparatus and a drowsiness-estimating method that improve the accuracy of drowsiness estimation by eliminating the influence of differences between individuals.

Solution to Problem

A drowsiness estimating apparatus according to an aspect of the present invention is an apparatus for estimating a drowsiness level of a subject of drowsiness estimation from among a plurality of drowsiness level candidates, the drowsiness estimating apparatus including: an acquisition section that acquires a drowsiness estimation parameter at each of a plurality of acquisition timings; a detecting section that detects an action of the subject of drowsiness estimation; a time-calculating section that calculates a recurrence required time which is the time it takes, from a detection timing at which the action is detected, for a value of the drowsiness estimation parameter acquired after the detection timing to return to a value of the drowsiness estimation parameter acquired before the detection timing; and an estimating section that estimates a drowsiness level of the subject of drowsiness estimation based on the calculated recurrence required time.

A drowsiness-estimating method according to an aspect of the present invention is a method that estimates a drowsiness level of a subject of drowsiness estimation from among a plurality of drowsiness level candidates, the drowsiness-estimating method including: acquiring a drowsiness estimation parameter at each of a plurality of acquisition timings; detecting an action of the subject of drowsiness estimation; calculating a recurrence required time which is the time it takes, from a detection timing at which the action is detected, for a value of the drowsiness estimation parameter acquired after the detection timing to return to a value of the drowsiness estimation parameter acquired before the direction timing; and estimating a drowsiness level of the subject of drowsiness estimation based on the calculated recurrence required time.

Advantageous Effects of Invention

According to the present invention, a drowsiness-estimating apparatus and a drowsiness-estimating method can be provided that improve the accuracy of drowsiness estimation by eliminating the influence of differences between individuals.

BRIEF DESCRIPTION OF DRAWINGS

FIG. 10 is a drawing showing an example of an adjustment table;

FIG. 13 is a drawing showing an example of an adjustment table.

DESCRIPTION OF EMBODIMENTS

Embodiments of the present invention are described below in detail, with references to drawings. In the embodiments, configuration elements that are the same are assigned the same reference signs, and the descriptions thereof, which would be repetitive, will be omitted.

Embodiment 1

[Configuration of Drowsiness-Estimating Apparatus 100]

Figure 1:
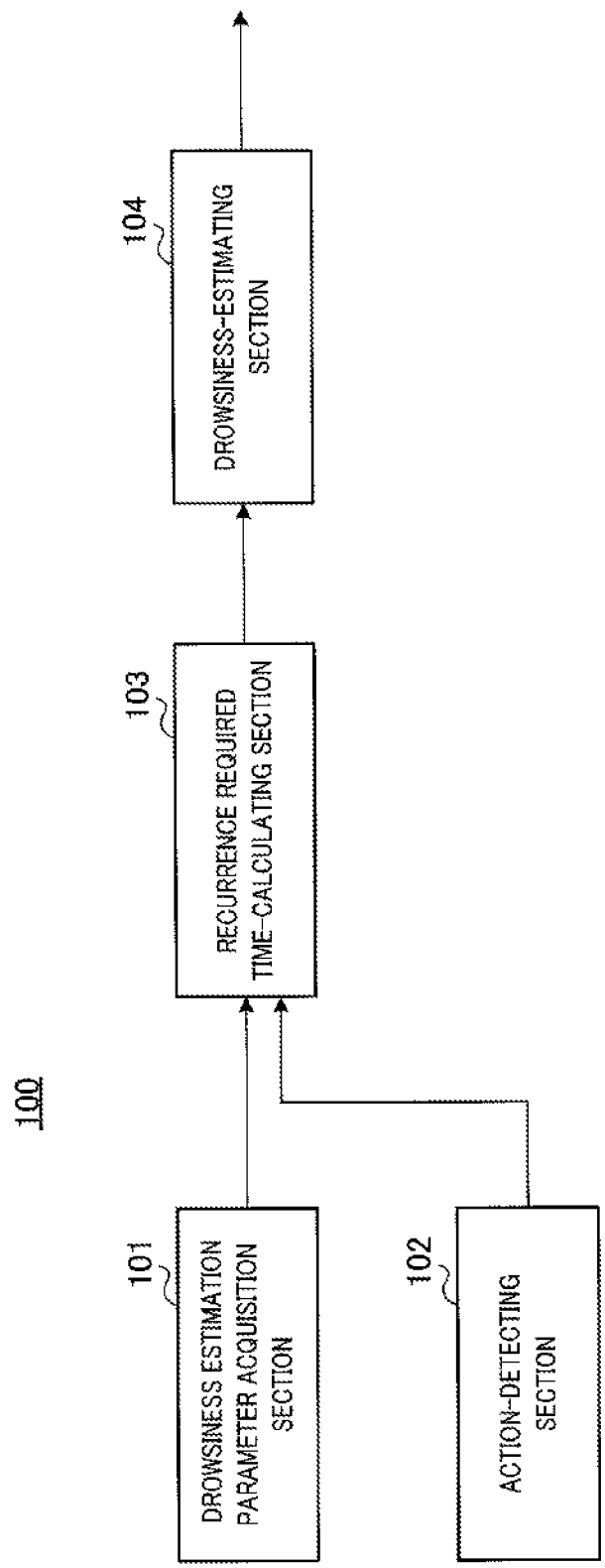
FIG. 1 is a block diagram showing the configuration of a drowsiness-estimating apparatus according to Embodiment 1 of the present invention.

FIG. 1 shows the configuration of drowsiness-estimating apparatus 100 according to Embodiment 1 of the present invention. Drowsiness-estimating apparatus 100 is mounted, for example, in a vehicle and implemented by an ECU (electronic control unit). In FIG. 1, drowsiness-estimating apparatus 100 has drowsiness estimation parameter acquisition section 101, action-detecting section 102, recurrence required time-calculating section 103, and drowsiness-estimating section 104.

Drowsiness estimation parameter acquisition section 101 acquires a "drowsiness estimation parameter" regarding a subject of drowsiness estimation (for example, a driver of a vehicle). A drowsiness estimation parameter is facial expression feature information, or the drowsiness level directly estimated from the facial expression feature information (hereinafter sometimes referred to as "rough drowsiness level"), or the like. Facial expression feature information is, for example, the distance between feature points on regions of the face or an image feature amount of the facial image.

Drowsiness estimation parameter acquisition section 101 acquires drowsiness estimation parameters at a prescribed interval and outputs them to recurrence required time-calculating section 103.

Action-detecting section 102 detects action of the detection subject and, if action is detected, outputs action detection information to recurrence required time-calculating section 103.

Recurrence required time-calculating section 103 acquires a drowsiness estimation parameter from drowsiness estimation parameter acquisition section 101 at a prescribed interval. If action has been detected by action-detecting section 102, recurrence required time-calculating section 103 acquires action detection information from action-detecting section 102.

Recurrence required time-calculating section 103 calculates the "recurrence required time" based on the drowsiness estimation parameter acquired before the acquisition timing of the action detection information, and the drowsiness estimation parameter acquired after the acquisition timing of the action detection information. The recurrence required time is the time it takes, from the detection timing at which the action is detected, for the value of the drowsiness estimation parameter acquired after the acquisition timing of the action detection information to return to the value of the drowsiness estimation parameter acquired before the acquisition timing of the action detection information (hereinafter sometimes referred to as the "reference value").

Specifically, recurrence required time-calculating section 103 starts measuring the time elapsed from the timing of the reception of the action detection information, and measures the time at which value of the drowsiness estimation parameter acquired after the acquisition timing of the action detection information reaches the reference value. The time measured in this manner is called the recurrence required time.

Drowsiness-estimating section 104 estimates the drowsiness level of the subject of drowsiness estimation, based on the recurrence required time calculated in recurrence required time-calculating section 103. Specifically, drowsiness-estimating section 104 has a drowsiness level estimation table in which each of a plurality of time ranges is associated with a drowsiness level. Drowsiness-estimating section 104 identifies a drowsiness level associated with a time range in the drowsiness level estimation table corresponding to the recurrence required time calculated in recurrence required time-calculating section 103. The identified drowsiness level is the drowsiness level estimated with regard to the subject of drowsiness estimation.

[Configuration of Safe Driving Support Apparatus 200]

Figure 2:
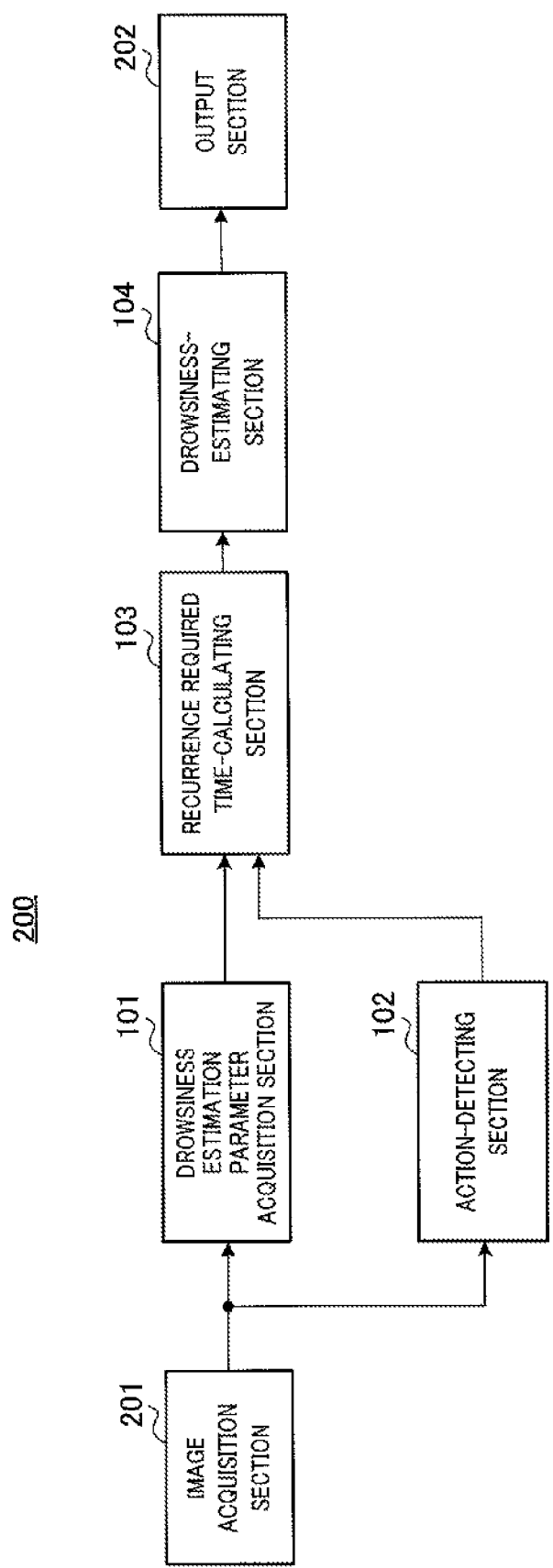
FIG. 2 is a block diagram showing the configuration of a safe driving support apparatus according to Embodiment 1 of the present invention.

FIG. 2 shows the configuration of safe driving support apparatus 200 according to Embodiment 1 of the present invention. Safe driving support apparatus 200 is configured so as to include drowsiness-estimating apparatus 100. In FIG. 2, safe driving support apparatus 200 has image acquisition section 201 and output section 202. As described above, in Embodiment 1, although it is possible to use either facial expression feature information or a rough drowsiness level as a drowsiness estimation parameter, in the following the configuration is described for the case of the drowsiness estimation parameter being facial expression feature information.

Image acquisition section 201 acquires a facial image of the driver of a vehicle at a prescribed interval, and outputs the facial image to drowsiness estimation parameter acquisition section 101 and action-detecting section 102. Image acquisition section 201 is, for example, a camera mounted in a vehicle and facing the driver. This camera captures an image in a region that includes the face of the driver.

Drowsiness estimation parameter acquisition section 101 acquires a drowsiness estimation parameter regarding the subject of drowsiness estimation (for example, the driver of a vehicle).

Figure 3:
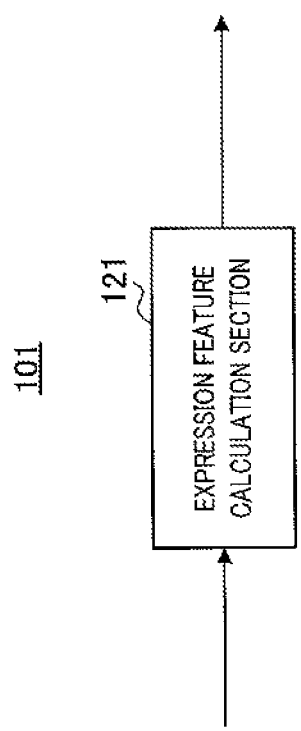
FIG. 3 is a block diagram showing the configuration of a drowsiness estimation parameter acquisition section.

FIG. 3 shows the configuration of drowsiness estimation parameter acquisition section 101 according to Embodiment 1 of the present invention. In FIG. 3, drowsiness estimation parameter acquisition section 101 has expression feature calculation section 121.

Expression feature calculation section 121, using the facial image output from image acquisition section 201, calculates the value of a drowsiness estimation parameter (that is, the facial expression feature information) with regard to a subject of drowsiness estimation (in this case, for example, the driver of a vehicle).

Specifically, if the distance between two feature points in a region of the face is used as the drowsiness estimation parameter, a pair of upper and lower eyelids, a pair of left and right eyelashes, or the left and right come of the mouth are used as the two feature points. Shape extraction, template matching, AAM (active appearance model), ASM (active shape model), or the like is used in detecting the feature points on a portion of the face.

If an image feature amount of a facial image is used as a drowsiness estimation parameter, as the image feature amount is obtained by applying Gabor feature, HoG (histogram of oriented gradient) feature, or a Haar-like feature with respect to a part of the facial image data (for example, the region between the eyebrows).

The value of a drowsiness estimation parameter calculated in this manner is output to recurrence required time-calculating section 103.

Action-detecting section 102, using a facial image output from image acquisition section 201, detects an action of the detection subject. For example, if the subject of drowsiness estimation is the driver of a vehicle, the action of the detection subject is movement of the eyes or head in order to check the rear-view mirror, a side mirror, an instrument, or the like. Action-detecting section 102, rather than using a facial image, may take the action of the detection subject to be speaking to operate equipment by voice input, or to converse with an occupant of the vehicle.

As described above, recurrence required time-calculating section 103 calculates the recurrence required time, based on a drowsiness estimation parameter acquired before the acquisition timing of the action detection information, and the drowsiness estimation parameter acquired after the acquisition timing of the action detection information. The recurrence required time is shorter, the deeper is the drowsiness of the subject of drowsiness estimation, and the longer is the drowsiness of the subject of drowsiness estimation lighter (that is, the closer the subject is to being awake).

Drowsiness-estimating section 104 estimates the drowsiness level of the subject of drowsiness estimation based on the recurrence required time calculated by recurrence required time calculating section 103. As described above, the estimation of the drowsiness level uses a drowsiness level estimation table in which each of a plurality of time ranges is associated with a drowsiness level candidate. In the drowsiness level estimation table, each time range is associated with a drowsiness level, which is higher, the shorter is the time that establishes the time range. That is, drowsiness-estimating section 104 estimates the drowsiness level of the subject of drowsiness estimation by identifying a drowsiness level candidate associated with a time range to which the recurrence required time calculated by recurrence required time-calculating section 103 belongs.

The drowsiness levels that are used can be, for example, the drowsiness levels established in Non-Patent Literature (hereinafter, referred to as "NPL") 1. In NPL 1, five steps of drowsiness level are established, these being level 1, which is no apparent drowsiness, level 2, which is apparently slightly sleepy, level 3, which is apparently sleepy, level 4, which is apparently quite sleepy, and level 5, which is apparently very sleepy. In the initial stages of drowsiness levels up to drowsiness level 3, supporting safe driving is said to be effective in preventing accidents.

Output section 202 outputs notification information responsive to the drowsiness level estimated by the drowsiness-estimating section 104. This notification information is output so as to prevent an accident due to drowsiness.

For example, at drowsiness level 1, output section 202 outputs nothing.

At drowsiness level 2, output section 202 uses an emphasized sound emphasizing the ambient sound in the vehicle compartment, a fragrance, cold air, light or the like as the notification information. Doing this unobtrusively enables the driver to be prompted to prevent drowsiness. In this case, output section 202 can be implemented by a speaker, a ventilator, LED illumination, or the like.

At drowsiness level 3, output section 202 uses an alarm sound (beep, voice, or ultrasonic), vibration of the seat or the steering wheel, short-term take-up of the seatbelt, or the like as the notification information. Doing this enables prompting of the attention of the driver.

At drowsiness level 4 or 5, output section 202 uses a high-volume alarm sound, a large vibration of the seat or steering wheel, or the like as the notification information. Simultaneously with this, safe driving support apparatus 200 may actively prompt the driver to take a rest. Also, for example, if the distance to a vehicle being followed is extremely short, safe driving support apparatus 200 may intervene in the control of the vehicle and make an emergency stop.

[Operation of Drowsiness-Estimating Apparatus 100]

Figure 4:
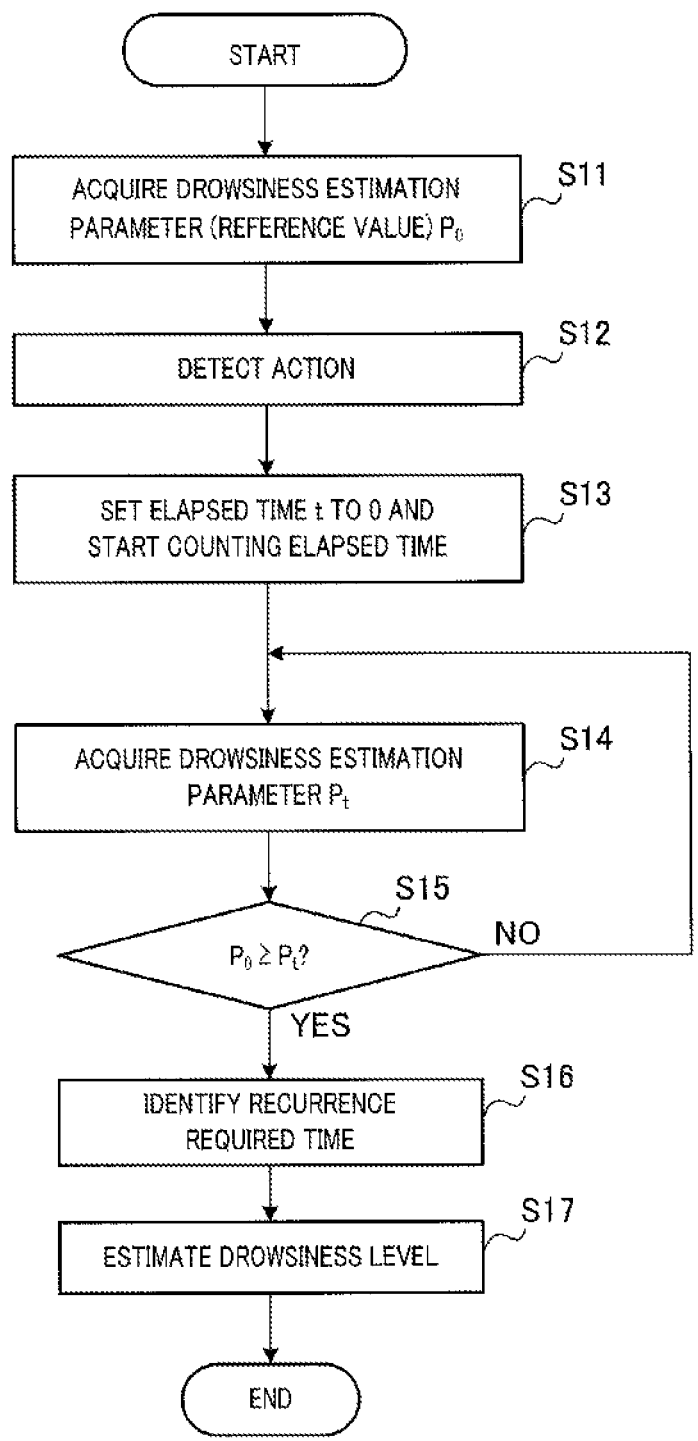
FIG. 4 is a flowchart provided to describe the operation of a drowsiness-estimating apparatus.

An example of the operation of drowsiness-estimating apparatus 100 having the above-described configuration will be described. FIG. 4 is a flowchart provided to describe the operation of drowsiness-estimating apparatus 100.

At step S11, drowsiness estimation parameter acquisition section 101 acquires a drowsiness estimation parameter (reference value) $P_0$ and outputs it to recurrence required time-calculating section 103.

At step S12, action-detecting section 102 detects an action of the detection subject and outputs action detection information to recurrence required time-calculating section 103. In this case, if the driver makes an action that is the subject of detection, the drowsiness level of the driver approaches level 1 (that is, the lowest drowsiness level) at least temporarily.

At step S13, recurrence required time-calculating section 103 receives the action detection information, resets the elapsed time t to zero, and also starts counting the elapsed time.

At step S14, drowsiness estimation parameter acquisition section 101 acquires a drowsiness estimation parameter $P_t$ and outputs it to recurrence required time-calculating section 103.

At step S15, recurrence required time-calculating section 103 judges whether or not $P_t$ is not greater than $P_0$. In this case, the description will be for the premise that, as the degree of drowsiness becomes higher, the drowsiness estimation parameter (for example, rough drowsiness level) will become larger, but depending upon the drowsiness estimation parameter that is used, the magnitude relationship between $P_0$ and $P_t$ used as a judgment condition might be reversed.

At step S15, if the judgment is made that $P_t$ is larger than $P_0$ (NO at step S15), drowsiness estimation parameter acquisition section 101 acquires the drowsiness estimation parameter $P_t$ at the next time at step S14.

At step S15, if the judgment is made that $P_t$ is not greater than $P_0$ (YES at step S15), recurrence required time-calculating section 103 identifies the elapsed time (that is, the recurrence required time) at that time at step S16.

At step S17, drowsiness-estimating section 104 estimates the drowsiness level of the subject of drowsiness estimation based on the recurrence required time identified at step S16.

According the present embodiment as described above, in drowsiness-estimating apparatus 100, recurrence required time-calculating section 103 calculates the recurrence required time which is the time it takes, from the detection timing at which the action is detected, for the value of the drowsiness estimation parameter acquired after the timing of the action detection to return to the value of the drowsiness estimation parameter acquired before the timing of the action detection, and drowsiness-estimating section 104 estimates the drowsiness level of the subject of drowsiness estimation based on the calculated recurrence required time.

Instead of a drowsiness estimation parameter that has variation by individual differences, it is possible in this manner to use the recurrence required time to estimate the drowsiness level, enabling estimation of the drowsiness level with the elimination of the influence of differences between individuals.

Specifically, drowsiness-estimating section 104 holds a drowsiness level estimation table, in which each of a plurality of time ranges is associated with a drowsiness level candidate, and identifies a drowsiness level candidate corresponding to a time range among the plurality of time ranges to which the recurrence required time belongs.

Embodiment 2

In Embodiment 1, estimation is performed with regard to all drowsiness levels using the recurrence required time. It is possible to use either facial expression feature information or rough drowsiness level as the drowsiness estimation parameter. In contrast, in Embodiment 2, the rough drowsiness level is used as the drowsiness estimation parameter. The accuracy is relatively high for even the rough drowsiness level, and at the highest level and lowest level, rather than performing estimation processing using the recurrence required time, the rough drowsiness level is used as is as the drowsiness level. Doing this enables a reduction of the processing load in the drowsiness-estimating apparatus.

[Configuration of Drowsiness-Estimating Apparatus 300]

Figure 5:
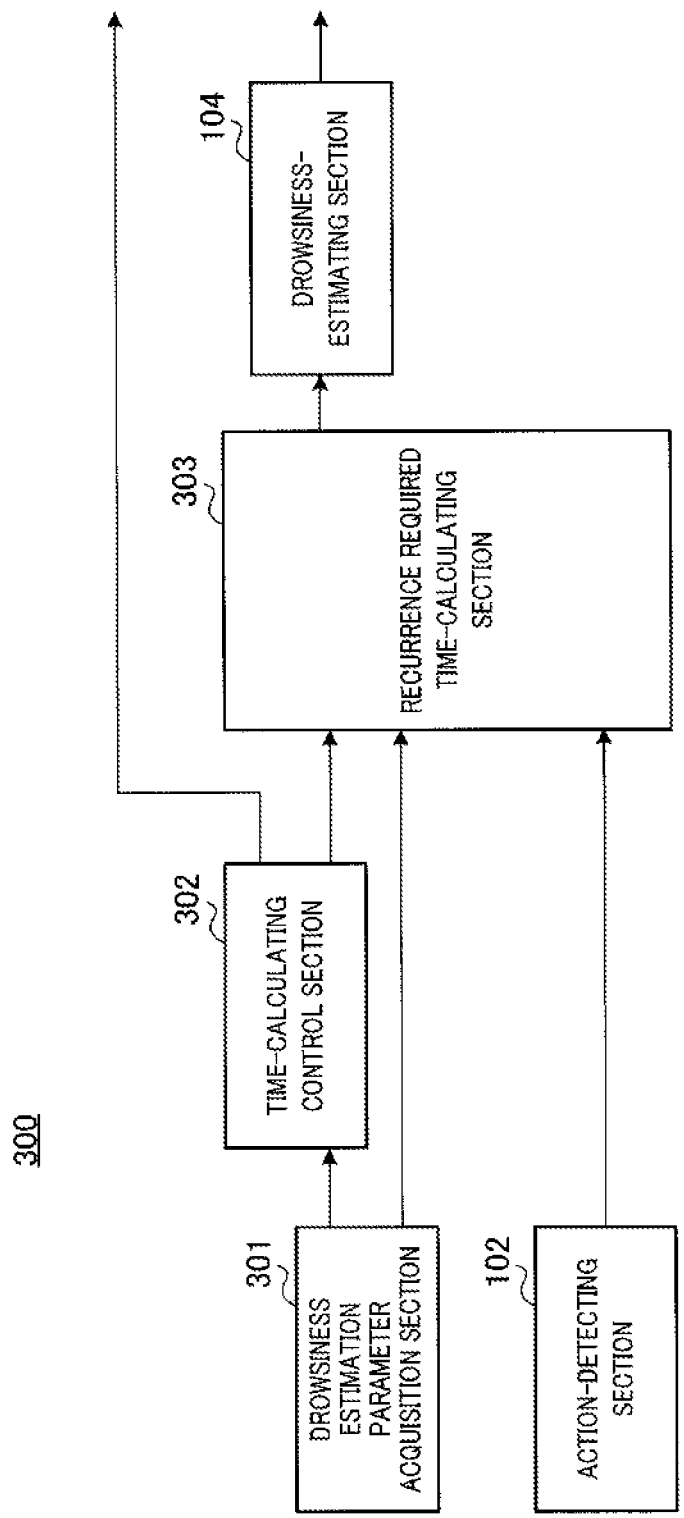
FIG. 5 is a block diagram showing the configuration of a drowsiness-estimating apparatus according to Embodiment 2 of the present invention.

FIG. 5 shows the configuration of drowsiness-estimating apparatus 300 according to Embodiment 2 of the present invention. In FIG. 5, drowsiness-estimating apparatus 300 has drowsiness estimation parameter acquisition section 301, time-calculating control section 302, and recurrence required time-calculating section 303.

Drowsiness estimation parameter acquisition section 301 acquires a drowsiness estimation parameter at a prescribed interval and outputs this to time-calculating control section 302 and recurrence required time-calculating section 303. In this case, the drowsiness estimation parameter is the rough drowsiness level.

Figure 6:
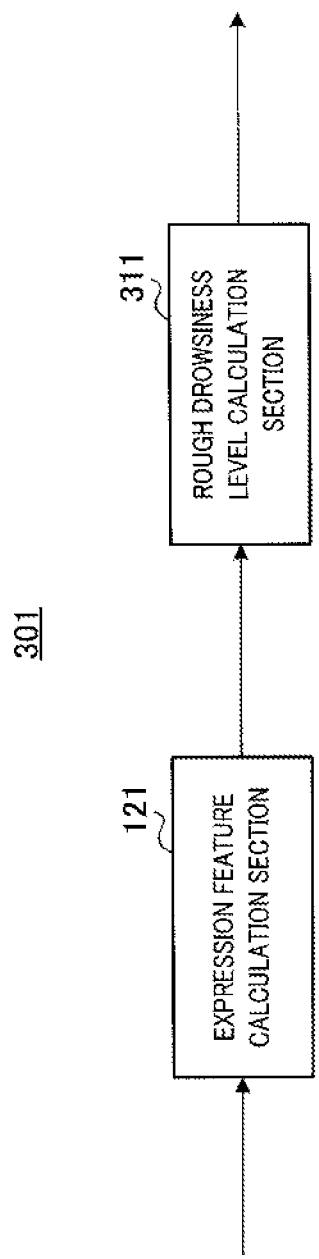
FIG. 6 is a block diagram showing the configuration of a drowsiness estimation parameter acquisition section.

FIG. 6 shows the configuration of drowsiness estimation parameter acquisition section 301 according to Embodiment 2 of the present invention. In FIG. 6, drowsiness estimation parameter acquisition section 301 has rough drowsiness level calculation section 311.

Rough drowsiness level calculation section 311 estimates the drowsiness level based on the facial expression feature information calculated in expression feature calculating section 121. The estimated drowsiness level is the rough drowsiness level. In order to distinguish the drowsiness level estimated in drowsiness-estimating section 104 with good accuracy, the drowsiness level estimated by rough drowsiness level calculation section 311 will be called the rough drowsiness level. Therefore, for example, five steps of level 1 to level 5 are prepared for the rough drowsiness level as well.

In this case, as the drowsiness level becomes high, the distance between the upper eyelid and the lower eyelid tends to become small, the distance between the left and right eyebrows tends to become large after becoming small, and the distance between the corners of the mouth tends to become small. Also, as the drowsiness level becomes high, a characteristic feature amount that appears as a texture having many high-frequency components is obtained as an image feature amount in the region between the eyebrows. This is due to wrinkles that appear between the eyebrows when a driver resists drowsiness and attempts to wake up as the drowsiness level becomes high.

Returning to FIG. 5, time-calculating control section 302, in response to the rough drowsiness level output from drowsiness estimation parameter acquisition section 301, controls the execution of the calculation processing by recurrence required time-calculating section 303. Specifically, if the rough drowsiness level output from the drowsiness estimation parameter acquisition section 301 is the highest level or the lowest level, time-calculating control section 302 outputs a calculation processing stop command signal to recurrence required time-calculating section 303 and also outputs to a subsequent functional part (for example output section 202) the rough drowsiness level as a drowsiness level having a high accuracy similar to the drowsiness level estimated at the drowsiness-estimating section 104. If, however, the rough drowsiness level output from drowsiness estimation parameter acquisition section 301 is a level other the highest nor the lowest level, time-calculating control section 302 outputs a calculation processing execution command signal to recurrence required time-calculating section 303.

Recurrence required time-calculating section 303 basically has the same function as recurrence required time-calculating section 103 of Embodiment 1. However, recurrence required time-calculating section 303 executes processing to calculate the recurrence required time only upon reception of an execution command signal from time-calculating control section 302. That is, recurrence required time-calculating section 303 executes processing to calculate the recurrence required time only when the rough drowsiness level is a level other than the highest level and the lowest level. This is because although identification of the drowsiness level 1, which represents the normal condition (that is, the awakened condition) and the drowsiness level 5, which represents the extremely sleepy condition is relatively easy, it is difficult to distinguish between drowsiness levels 2 to 4, which correspond to the period from the initial period to the middle period of drowsiness level.

[Operation of Drowsiness-Estimating Apparatus 300]

Figure 7:
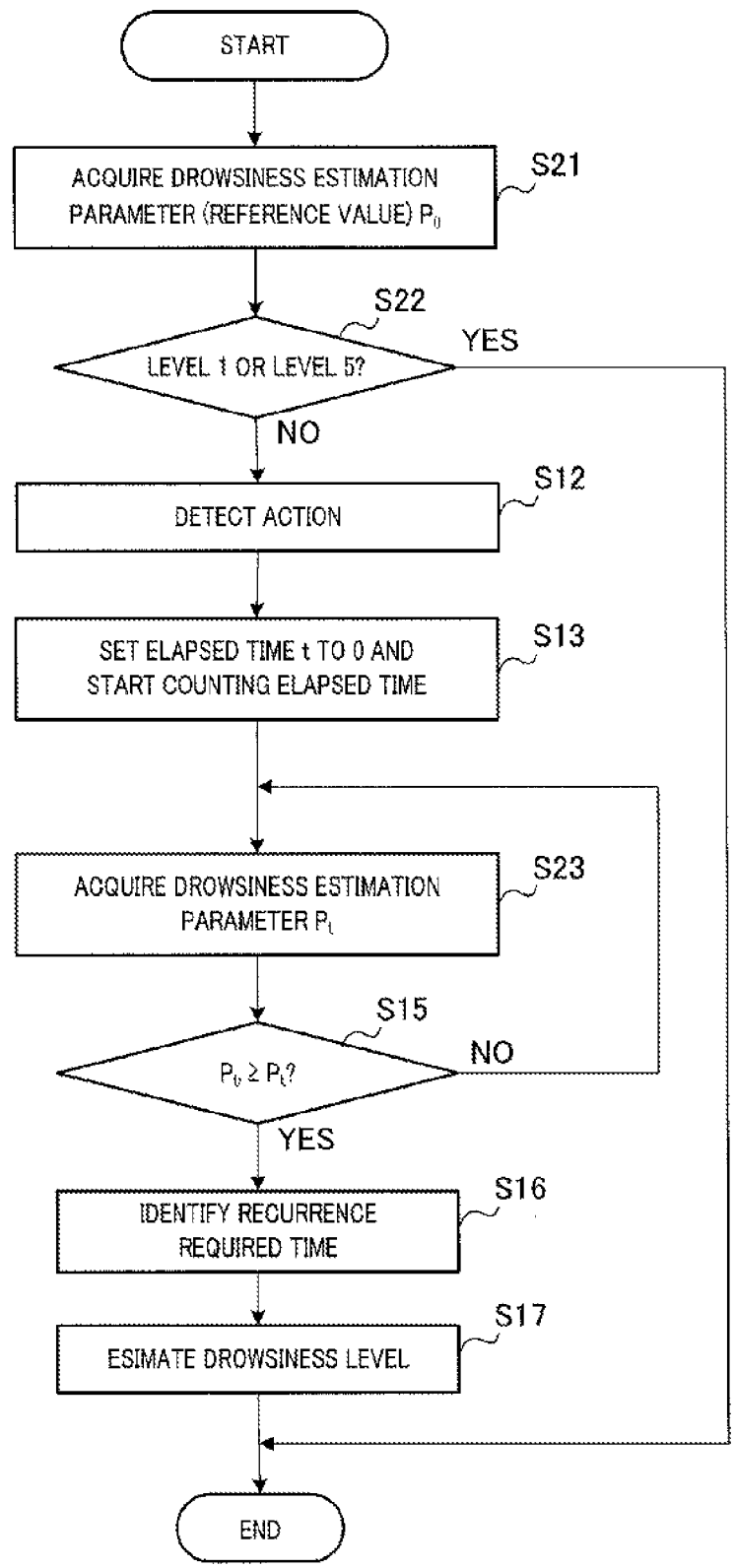
FIG. 7 is a flowchart provided to describe the operation of a drowsiness-estimating apparatus.

FIG. 7 is a flowchart provided to describe the operation of drowsiness-estimating apparatus 300.

At step S21, drowsiness estimation parameter acquisition section 301 acquires the drowsiness estimation parameter (reference value) $P_0$ and outputs it to time-calculating control section 302 and recurrence required time-calculating section 303. In this case, the drowsiness estimation parameter is the rough drowsiness level.

At step S22, time-calculating control section 302 judges whether or not the rough drowsiness level output from drowsiness estimation parameter acquisition section 301 is level 1 or level 5.

If the judgment is made at step S22 that the rough drowsiness level is either level 1 or level 5 (YES at step S22), time-calculating control section 302 outputs a calculation processing stop command signal to recurrence required time-calculating section 303. Doing this ends the drowsiness level estimation processing.

If the judgment is made at step S22 that the rough drowsiness level is neither level 1 nor level 5 (NO at step S22), time-calculating control section 302 outputs a calculation processing execution command signal to recurrence required time-calculating section 303.

At step S23, drowsiness estimation parameter acquisition section 301 acquires the drowsiness estimation parameter $P_t$ and outputs it to time-calculating control section 302 and recurrence required time-calculating section 303.

According to the present embodiment as described above, in drowsiness-estimating apparatus 300, drowsiness estimation parameter acquisition section 301 calculates the rough drowsiness level as the drowsiness estimation parameter based on the distance between feature points on a region of the face of the subject of drowsiness estimation or on an image feature amount of the facial image, and recurrence required time-calculating section 303 calculates the recurrence required time only when the rough drowsiness level corresponds to a drowsiness level candidate other than the highest and lowest drowsiness levels among the plurality of drowsiness level candidates.

Because the recurrence required time is calculated for only a drowsiness level candidate other than the highest and lowest drowsiness level candidates among the plurality of drowsiness level candidates, the levels of which are difficult to distinguish, doing this can reduce the processing load on drowsiness-estimating apparatus 300.

Embodiment 3

[Configuration of Drowsiness-Estimating Apparatus 400]

Figure 8:
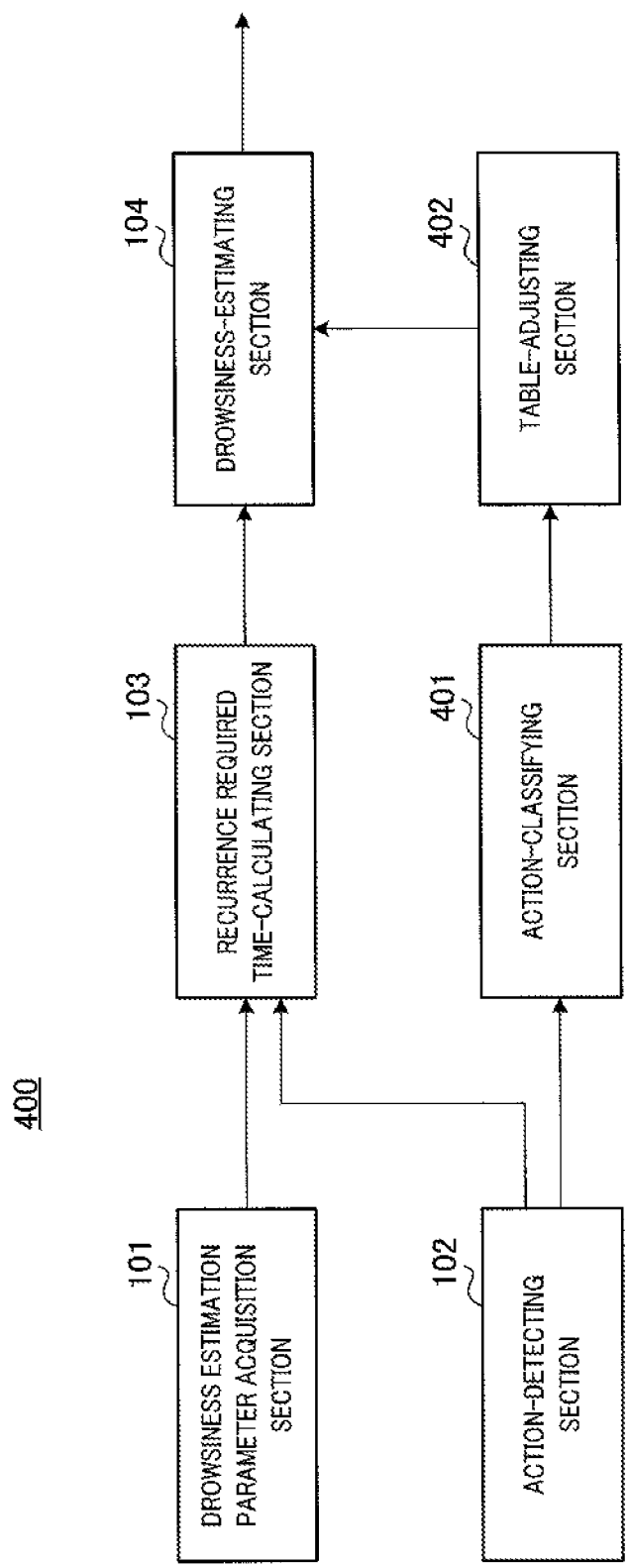
FIG. 8 is a block diagram showing the configuration of a drowsiness-estimating apparatus according to Embodiment 3 of the present invention.

FIG. 8 shows the configuration of drowsiness-estimating apparatus 400 according to Embodiment 3 of the present invention. In FIG. 8, drowsiness-estimating apparatus 400 has action-classifying section 401 and table-adjusting section 402.

Action-classifying section 401 classifies an action detected by action-detecting section 102 into a plurality of classes based on an action classification parameter. The action classification parameter in Embodiment 3 represents the size of eye movement or head behavior, which corresponds to the action, as the size of time changes of the eye angle or head angle.

In this case, a coordinate system is defined with the z axis in the vertical direction with respect to the center of the head of the driver, the x axis in the front direction from the center of the eyes of the driver, and the y axis along a straight line joining the eyes in the direction perpendicular with respect to the x axis. In this coordinate system, for example, when verifying an instrument with only a change of the eye direction, the movement of the pitch direction of the eye direction over a short period of time (up/down movement of approximately 20° in approximately 0.5 sec), without a change of the head angle, is sensed. In this case, therefore, action-classifying section 401 classifies into an action class having a small driving action. Also, for example, when the driver's seat is on the right side and the left side mirror is viewed, there is a yaw-direction change over a short period of time (approximately 1 sec) in the angle of the head (approximately 30° in the yaw direction) and the eye direction (30° in the yaw direction). In making a lane change, when the neck is rotated to visually check behind and to the side, the head angle is sensed as rotation in the yaw direction (rotating movement of approximately 90° in approximately 2 sec). In this case, action-classifying section 401 classifies into an action class having a large driving action.

Table-adjusting section 402, in response to the class into which the action detected by the action-detecting section 102 is classified by action-classifying section 401, adjusts the drowsiness level estimation table used by drowsiness-estimating section 104.

Specifically, table-adjusting section 402 adjusts the time defining each time range in the drowsiness level estimation table used by drowsiness-estimating section 104 (that is, the threshold) in response to the class into which the action detected by action-detecting section 102 was classified by action-classifying section 401. Instead of adjusting the threshold in one drowsiness level estimation table, drowsiness-estimating section 104 may be made to hold a plurality of drowsiness level estimation tables, and table-adjusting section 402 may specify a table, among the plurality of drowsiness level estimation tables, in accordance with the class classified by action-classifying section 401.

[Operation of Drowsiness-Estimating Apparatus 400]

Figure 9:
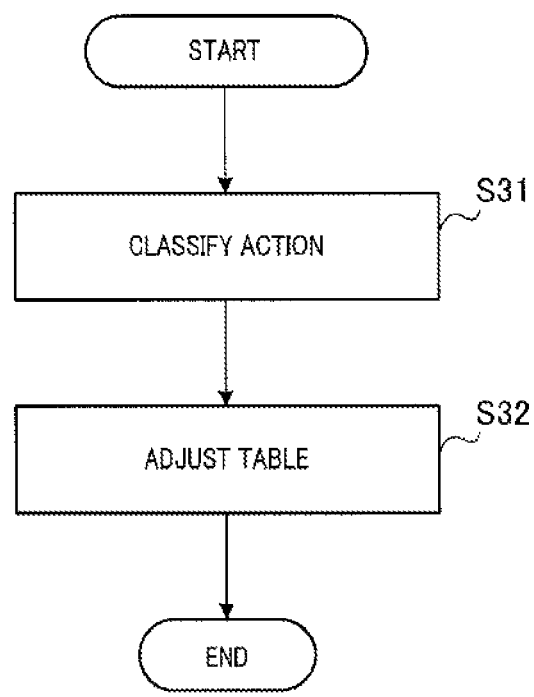
FIG. 9 is a flowchart provided to describe table adjustment processing.

FIG. 9 is a flowchart provided to describe the table adjustment processing in drowsiness-estimating apparatus 400.

At step S31, action-classifying section 401 classifies actions detected by action-detecting section 102 into classes, based on the "action classification parameter." The action classification parameter in Embodiment 3 represents the size of eye direction movement or head behavior corresponding to the action as the size of a time change in the eye angle or head angle.

Action-classifying section 401 classifies into classes of "large," "medium," and "small," based on the size of the driving action.

At step S32, table-adjusting section 402 adjusts the drowsiness level estimation table used by drowsiness-estimating section 104, in accordance with the class into which the action detected by action-detecting section 102 is classified by action-classifying section 401. This table adjustment is performed based on an adjustment table.

FIG. 10 shows an example of an adjustment table. In FIG. 10, $t\_1$ is a threshold that divides drowsiness level 4 and drowsiness level 3, $t\_2$ is a threshold that divides drowsiness level 3 and drowsiness level 2, and $t\_3$ is a threshold that divides drowsiness level 2 and drowsiness level 1. Additionally, $a\_1$, $a\_2$, and $a\_3$ correspond respectively to the values of $t\_1$, $t\_2$, and $t\_3$ for the case in which classification is made into the "small" class, $b\_1$, $b\_2$, and $b\_3$ correspond respectively to the values of $t\_1$, $t\_2$, and $t\_3$ for the case in which classification is made into the "medium" class, and $c\_1$, $c\_2$, and $c\_3$ correspond respectively to the values of $t\_1$, $t\_2$, and $t\_3$ for the case in which classification is made into the "large" class. In this case, the values of $t\_1$, $t\_2$, and $t\_3$ according to the classes satisfy the following relationships.

$$0 < a\_1 \le b\_1 \le c\_1$$

$$0 < a\_2 \le b\_2 \le c\_2$$

$$0 < a\_3 \le b\_3 \le c\_3$$

$$0 < a\_1 < a\_2 < a\_3$$

$$0 < b\_1 < b\_2 < b\_3$$

$$0 < c\_1 < c\_2 < c\_3$$

Although the foregoing description cites as examples of a driving action the example of visual verification of an instrument, visual verification of the left side mirror, and visual verification behind and to the side when changing lanes, which are accompanied by movement of the eye direction and head behavior, other visual verifications by the driver of the existence of other moving objects (other vehicles or pedestrians) in the field of view around the vehicle with the vehicle forward direction taken as the center, or verification of the current indication of a traffic light or visual verification of the indication of a display or marker or the like may be the driving action. Additionally, momentarily strongly closing the eyes, striking the cheek, pinching the cheek, puffing out the cheeks, strong pulling the corners of the mouth, or twisting the neck or the like may be voluntary actions by the driver to resist drowsiness.

According to the present embodiment as described above, in drowsiness-estimating apparatus 400, action-classifying section 401, classifies an action detected by action-detecting section 102 into one of a plurality of classes, based on an action classification parameter, and table-adjusting section 402 adjusts the time defining each time range in the drowsiness level estimation table, in accordance with the classified class. The action classification parameter is the size of the detected action.

This enables adjustment of the drowsiness level estimation table in accordance with the size of the action that influences the recurrence required time, thereby improving the drowsiness estimation accuracy.

Embodiment 4

[Configuration of Drowsiness-Estimating Apparatus 500]

Figure 11:
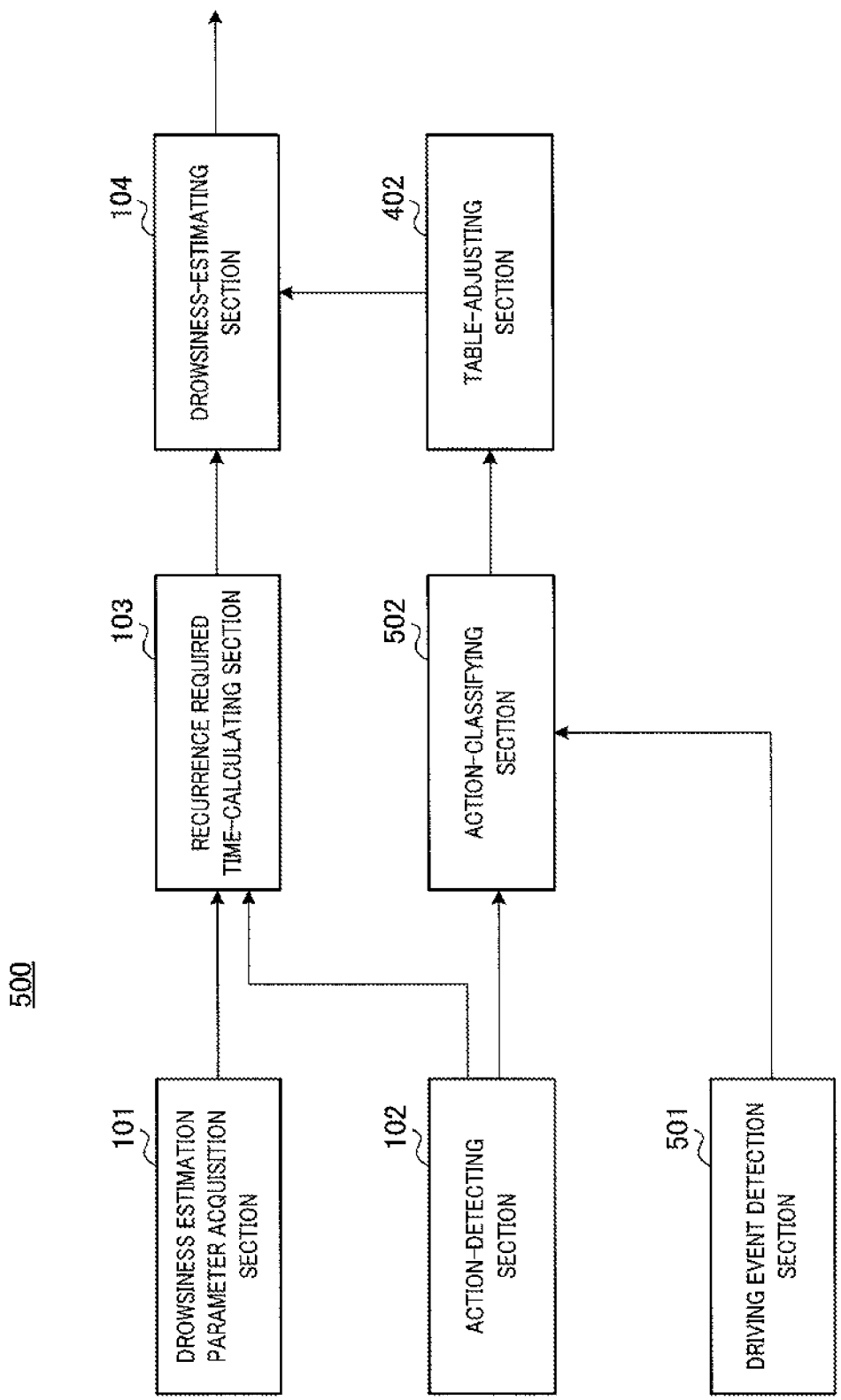
FIG. 11 is a block diagram showing the configuration of a drowsiness-estimating apparatus according to Embodiment 4 of the present invention.

FIG. 11 shows the configuration of drowsiness-estimating apparatus 500 according to Embodiment 4 of the present invention. In FIG. 11, drowsiness-estimating apparatus 500 has driving event detection section 501 and action-classifying section 502.

Driving event detection section 501 detects an "action classification parameter." In Embodiment 4, the "action classification parameter" is the frequency of occurrence of an event that evokes an action. The frequency of occurrence of the event is detected, for example, based on prompts and warnings from a warning lamp or a system such as a safe driving support system or navigation system, or based on an operational log of route guidance information output in real time.

Action-classifying section 502 classifies actions detected by action-detecting section 102 into a plurality of classes, based on the "action classification parameter" detected by driving event detection section 501.

Table-adjusting section 402 adjusts the drowsiness level estimation table used by drowsiness-estimating section 104 in accordance with the class that is classified by action-classifying section 502.

[Operation of Drowsiness-Estimating Apparatus 500]

Figure 12:
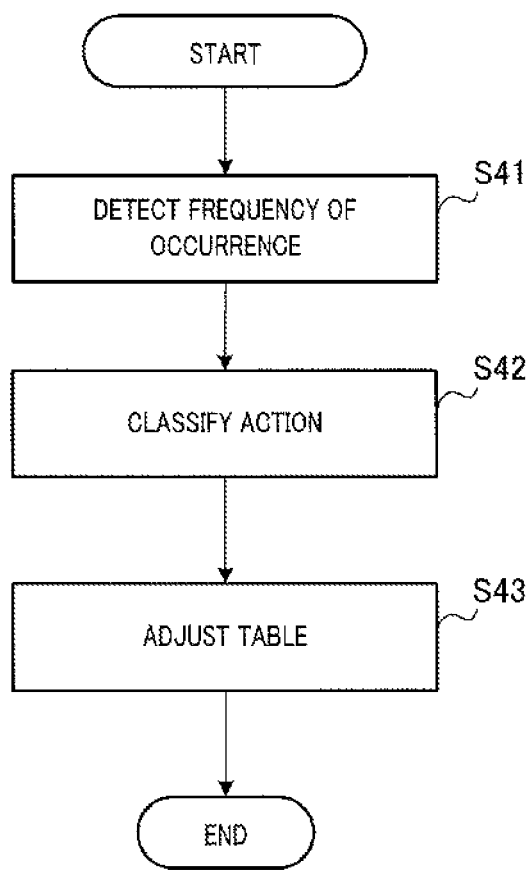
FIG. 12 is a flowchart provided to describe the table adjustment processing.

FIG. 12 is a flowchart provided to describe the table adjustment processing in drowsiness-estimating apparatus 500.

At step S41, driving event detection section 501 detects an "action classification parameter." In Embodiment 4, the "action classification parameter" is the frequency of occurrence of an event that evokes an action.

At step S42, action-classifying section 502 classifies the action detected by action-detecting section 102 into a class of a plurality of classes, based on the action classification parameter.

Action-classifying section 502 classifies, for example, into the three classes of "no driving event detected," and frequencies of occurrence of a driving event of "high" and "low."

At step S43, table-adjusting section 402 adjusts the drowsiness level estimation table used by drowsiness-estimating section 104, in accordance with the class of classification by action-classifying section 502. This table adjustment is done based on the adjustment table.

FIG. 13 shows an example of the adjustment table. In FIG. 13, $t\_1$ is a threshold that divides drowsiness level 4 and drowsiness level 3, $t\_2$ is a threshold that divides drowsiness level 3 and drowsiness level 2, and $t\_3$ is a threshold that divides drowsiness level 2 and drowsiness level 1. Additionally, $d\_1$, $d\_2$, and $d\_3$ correspond, respectively, to the values of $t\_1$, $t\_2$, and $t\_3$ for the case of the classification as the "no driving event detected" class. Also, $e\_1$, $e\_2$, and $e\_3$ correspond, respectively, to the values of $t\_1$, $t\_2$, and $t\_3$ for the case of the classification as the "high" class, and $f\_1$, $f\_2$, and $f\_3$ correspond, respectively, to the values of $t\_1$, $t\_2$, and $t\_3$ for the case of the classification as the "low" class. The values of $t\_1$, $t\_2$, and $t\_3$ according to the class satisfy the following relationships.

$$0<d\_1\le e\_1\le f\_1$$

$$0<d\_2\le e\_2\le f\_2$$

$$0<d\_3\le e\_3\le f\_3$$

$$0<d\_1<d\_2<d\_3$$

$$0<e\_1<e\_2<e\_3$$

$$0<f\_1<f\_2<f\_3$$

In the foregoing description, detection is done of the frequency of occurrence of an event based on prompts and warnings from a warning lamp or a system such as a safe driving support system or navigation system, or based on an operational log of route guidance information output in real time. This is, however, not a restriction, and driving event detection section 501 may be implemented by a microphone, so as to detect a horn from a nearby vehicle as an event. A driving action evoked by a horn is classified as a low-frequency event. Also, driving event detection section 501 may be implemented by a camera, thereby enabling detection of entering sunlight from the West. A driving action such as lowering the sun visor in response to being blinded by sunlight from the West is classified as a high-frequency event.

According to the present embodiment as described above, in drowsiness-estimating apparatus 500, action-classifying section 502 classifies an action detected by action-detecting section 102 into one of a plurality of classes, based on an action classification parameter, and table-adjusting section 402 adjusts the time defining each time range of the drowsiness level estimation table, in accordance with the classified class. The action classification parameter is the frequency of occurrence of an event that evokes an action, which is detected by driving event detection section 501.

This enables adjustment of the drowsiness level estimation table in accordance with the type of action that influences the recurrence required time, thereby improving the drowsiness estimation accuracy.

Other Embodiments (1) In the foregoing embodiments, action-detecting section 102 has been described as detecting an action using a facial image. However, this is not a restriction, and an action may be detected using the steering angle or the throttle opening angle obtained from a CAN (Controller Area Network), or an action may be detected using the size of the time variation of the pressure distribution of a seat sensor mounted to the driver's seat.

(2) Although the embodiments have been described taking a case in which the present invention is formed by hardware as an example, it is also possible to realize the present invention by software in conjunction with hardware.

Each function block employed in the description of the above embodiments may typically be implemented as an LSI formed by an integrated circuit. These may be individual chips or partially or totally contained on a single chip. The term "LSI" is adopted here, but this may also be referred to as "IC," "system LSI," "super LSI," or "ultra LSI" depending on differing extents of integration.

Further, the method of circuit integration is not limited to an LSI, and implementation using dedicated circuitry or general purpose processors is also possible. After LSI manufacture, utilization of an FPGA (field programmable gate array), which is programmable, or a reconfigurable processor that enables reconfiguration of connections or settings of circuit cells within an LSI is also possible.

Further, if integrated circuit technology emerges that replaces LSIs as a result of the advancement of semiconductor technology or a derivative other technology, naturally it is also possible to carry out function block integration using such technology. Application of biotechnology or the like is also possible.

The disclosure of the specification, drawings, and abstract included in Japanese Patent Application No. 2011-117834, filed on May 26, 2011, is incorporated herein by reference in its entirety.

INDUSTRIAL APPLICABILITY

The drowsiness-estimating apparatus and drowsiness-estimating method of the present invention are useful in that the apparatus and the method can improve the accuracy of drowsiness estimation by eliminating the influence of differences between individuals.

REFERENCE SIGNS LIST 100, 300, 400, 500 Drowsiness-estimating apparatus
101, 301 Drowsiness estimation parameter acquisition section
102 Action-detecting section
103, 303 Recurrence required time-calculating section
104 Drowsiness-estimating section
121 Expression feature calculation section
200 Safe driving support apparatus
201 Image acquisition section
202 Output section
302 Time-calculating control section
311 Rough drowsiness level calculation section
401, 502 Action-classifying section
402 Table-adjusting section
501 Driving event detection section

The invention claimed is:

1. A drowsiness estimating apparatus for estimating a drowsiness level of a subject of drowsiness estimation from among a plurality of drowsiness level candidates, the drowsiness estimating apparatus comprising:
an acquisition section that acquires a drowsiness estimation parameter at each of a plurality of acquisition timings;
a detecting section that detects an action of the subject of drowsiness estimation;
a time-calculating section that calculates a recurrence required time which is the time it takes, from a detection timing at which the action is detected, for a value of the drowsiness estimation parameter acquired after the detection timing to return to a value of the drowsiness estimation parameter acquired before the detection timing; and
an estimating section that estimates a drowsiness level of the subject of drowsiness estimation based on the calculated recurrence required time.

2. The drowsiness estimating apparatus according to claim 1, wherein:
the acquisition section comprises a level calculation section that calculates a second drowsiness level as the drowsiness estimation parameter based on face expression feature information of the subject of drowsiness estimation; and
the time-calculating section calculates the recurrence required time only when the second drowsiness level is associated with a drowsiness level candidate other than the highest and lowest drowsiness levels among the plurality of the drowsiness level candidates.

3. The drowsiness-estimating apparatus according to claim 1, wherein the estimation section holds a drowsiness level estimation table in which a plurality of time ranges are associated with the drowsiness level candidates, respectively, and the estimation section identifies a drowsiness level candidate corresponding to a time range to which the calculated recurrence required time belongs from among the plurality of time ranges.

4. The drowsiness-estimating apparatus according to claim 3, further comprising:
an action-classifying section that classifies an action detected by the detection section into one of a plurality of classes based on an action classification parameter; and
a table-adjusting section that adjusts a time defining each of the time ranges of the drowsiness level estimation table in accordance with the class of classification.

5. The drowsiness-estimating apparatus according to claim 4, wherein the action classification parameter is a size of the detected action.

6. The drowsiness-estimating apparatus according to claim 4, wherein the action classification parameter is a frequency of occurrence of an event that evokes the detected action.

7. A drowsiness-estimating method that estimates a drowsiness level of a subject of drowsiness estimation from among a plurality of drowsiness level candidates, the drowsiness-estimating method comprising:
acquiring a drowsiness estimation parameter at each of a plurality of acquisition timings;
detecting an action of the subject of drowsiness estimation;
calculating a recurrence required time which is the time it takes, from a detection timing at which the action is detected, for a value of the drowsiness estimation parameter acquired after the detection timing to return to a value of the drowsiness estimation parameter acquired before the direction timing; and
estimating a drowsiness level of the subject of drowsiness estimation based on the calculated recurrence required time.

* * * * *